United States Patent [19]

Keller, Jr. et al.

[11] 4,211,235
[45] Jul. 8, 1980

[54] PROGRAMMER FOR IMPLANTED PACER

[75] Inventors: John W. Keller, Jr., Miami, Fla.; Dennis Digby, Brooklyn Park; Alan Coombes, New Hope, both of Minn.

[73] Assignee: Biotronik Mess-lund Therapiegerate GmbH & Co., Berlin, Fed. Rep. of Germany

[21] Appl. No.: 917,139

[22] Filed: Jun. 19, 1978

[30] Foreign Application Priority Data

Aug. 19, 1977 [GB] United Kingdom ............... 34912/77

[51] Int. Cl.² .............................................. A61N 1/36
[52] U.S. Cl. ............................................. 128/419 PG
[58] Field of Search .................... 128/419 PG, 419 PT

[56] References Cited

U.S. PATENT DOCUMENTS

| 3,833,005 | 9/1974 | Wingrove | 128/419 PG |
| 3,932,816 | 1/1976 | MacGregor | 328/61 |
| 3,952,750 | 4/1976 | Mirowski et al. | 128/419 D |
| 4,024,875 | 5/1977 | Putzke | 128/419 PG |
| 4,049,004 | 9/1977 | Walters | 128/419 PG |
| 4,049,953 | 9/1977 | Evans | 235/150.3 |

Primary Examiner—William E. Kamm
Attorney, Agent, or Firm—Spencer & Kaye

[57] ABSTRACT

A plurality of programming bits are placed into a parallel in-serially out register. When the programmer is activated, a monostable resets a counter, and energizes an oscillator which clocks the counter. Three subintervals from the counter are utilized for pulse width modulation of the programming signals. Once for each bit, the output is energized and begins transmitting pulses at the lowest subinterval rate. Depending upon the logic state of each bit, the transmission pulse is terminated either at the second or the third subinterval time.

5 Claims, 3 Drawing Figures

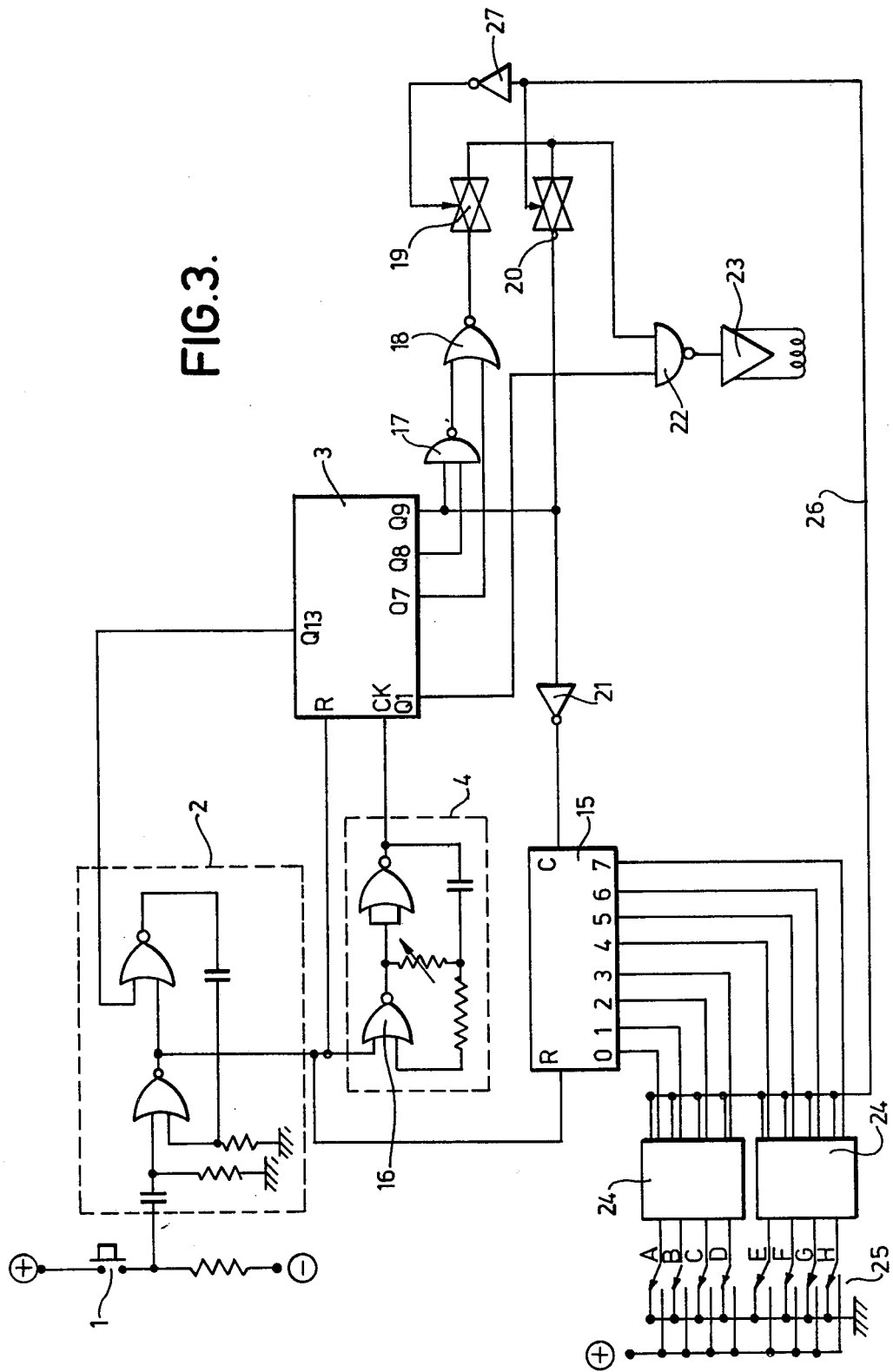

PROGRAMMER FOR IMPLANTED PACER

FIELD OF THE INVENTION

This invention relates to an apparatus for transmitting a preselected signal comprising a sequence of signal bits of different values. Such an apparatus can be termed a programmable transmitter where the signal it is desired to transmit to a receiver may be selected, or set, prior to transmission. The invention is especially concerned with programmable transmitters for enabling programming signals to be transmitted to, and received by, implanted, programmable body function control apparatus such as cardiac pacemakers.

BACKGROUND OF THE INVENTION

Pacemakers for generating artificial stimulating pulses for the heart, and which may be implanted in the body, are well known. Originally the electrical circuitry for such pacemakers was of analog design, but in recent years digital circuitry has been also employed. A digital approach to pacemakers has led to the evolution of programmable pacemakers—pacemakers having parameters such as pulse rates which are adjustable (programmable) once the pacemaker has been implanted. Programmable pacemakers are described in, for instance, British Specifications Nos. 1,385,954 and 1,398,875. Such pacemakers have circuitry to detect and decode signals transmitted outside the body and alter the program accordingly. In British Specification No. 1,385,954 (claiming priority based on U.S. Ser. No. 141694, in turn a parent of U.S. Pat. No. 3,805,796 to Tenz) the programming is accomplished by means of a magnetic field which is sensed by a magnetic reed switch; the opening and closing of the switch provides programming pulses to a program store. In British Specification No. 1,398,875 (based on U.S. Pat. No. 3,833,005 to Wingrove) the programming is by means of radio frequency transmission and reception.

Although much attention has been paid to the development of the implantable programmable pacemaker, there is also a need for an external programmable transmitter which can be programmed with the pacemaker program and this program then accurately transmitted to the implanted pacemaker.

We have now developed a programmable transmitter for such use.

SUMMARY OF THE INVENTION

According to the invention we provide an external programmer for supplying a fixed number of pulse-width modulated signal bits as a program to an implanted, programmable body function control apparatus which comprises means for preselecting and storing a fixed number of signal bits in a code representative of the program to be supplied to said implanted apparatus and for supplying said code as an output of said means when actuated, counter means for actuating the said code output, means for actuating the counter, and means responsive to said code output for transmitting said program to said implanted apparatus as a sequence of a said fixed number of pulse-width modulated signal bits.

BRIEF DESCRIPTION OF THE DRAWINGS

Preferred features of the invention will now be described, by way of example, with reference to the accompanying drawings, in which:

FIG. 3 shows schematically the electrical circuit diagram of an alternative embodiment.

DESCRIPTION OF THE PREFERRED EMBODIMENTS

The illustrated programmer is designed to transmit an 8-bit tone burst modulated program, that is, an 8-bit pulse width modulated signal where a sine wave carrier frequency is pulse width modulated by each of the 8 data bits.

Figure 1:
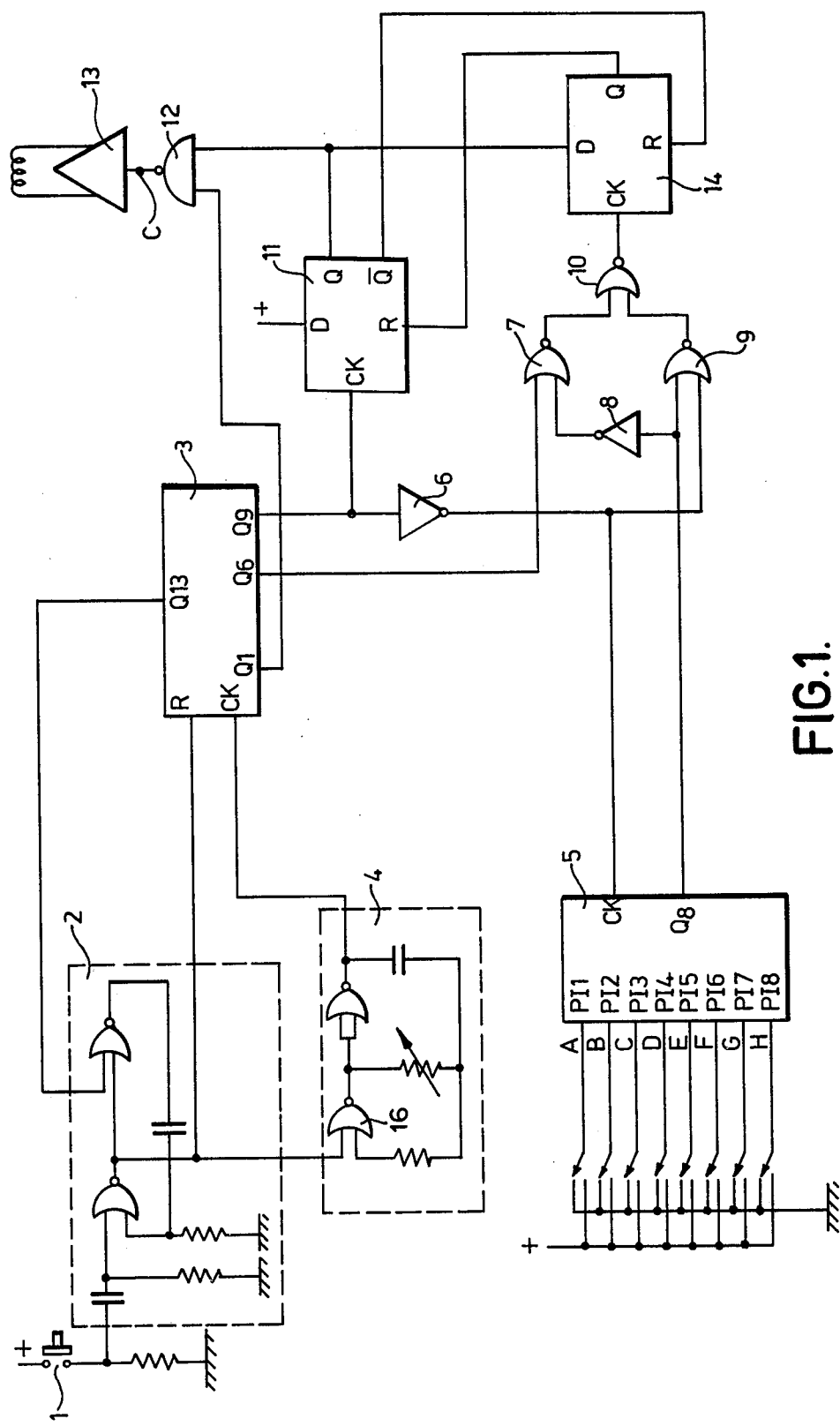
FIG. 1 shows schematically the electrical circuit diagram of an external programmer for encoding an 8-bit program, and for transmitting the program to an implanted, programmable cardiac pacemaker.

Referring to FIG. 1, the programmer comprises a "press-to-program" switch 1 tied between the positive voltage supply bus and ground. The switch output drives a monostable 2. The monostable 2 is employed to reset a 13 stage counter 3, and to control an oscillator 4. The oscillator 4 includes an "oscillator disable" NOR gate 16 on its input side which, when supplied with a high input from monostable 2, provides a low output which disables the oscillator output to a clock input of counter 3.

Only the Q1, Q6, Q9, and Q13 stages of counter 3 are employed. Stage Q9 is employed to clock a parallel in/serial out eight bit shift register 5 via an inverter 6. The eight parallel inputs for shift register 5 (PI 1 to 8) are labelled A to H and the values of such inputs are set by eight switches which individually can be connected to the positive supply bus or to ground.

The outputs from the Q6 stage of counter 3, inverter 6, and the serial output Q8 of shift register 5 drive a pulse steering network composed of NOR gates 7, 9, and 10 and inverter 8.

The Q9 stage of counter 3 also clocks a D-type flip-flop 11 whose D-input is tied to the positive supply bus. The Q output of flip-flop 11 is supplied to one input of a NAND gate 12, whose second input is supplied by the Q1 stage of counter 3. NAND gate 12 drives an amplifier/transmitter 13, outputs from which are transmitted into the body for receipt by an implanted cardiac pacemaker where the received pulses are decoded and employed for changing the program stored in the pacemaker.

The output of NOR gate 10 clocks a further D-type flip-flop 14, whose D-input and reset are driven by the Q and $\overline{Q}$ outputs, respectively, of flip-flop 11. The Q output of flip-flop 14 is employed to reset flip-flop 11.

Figure 2:
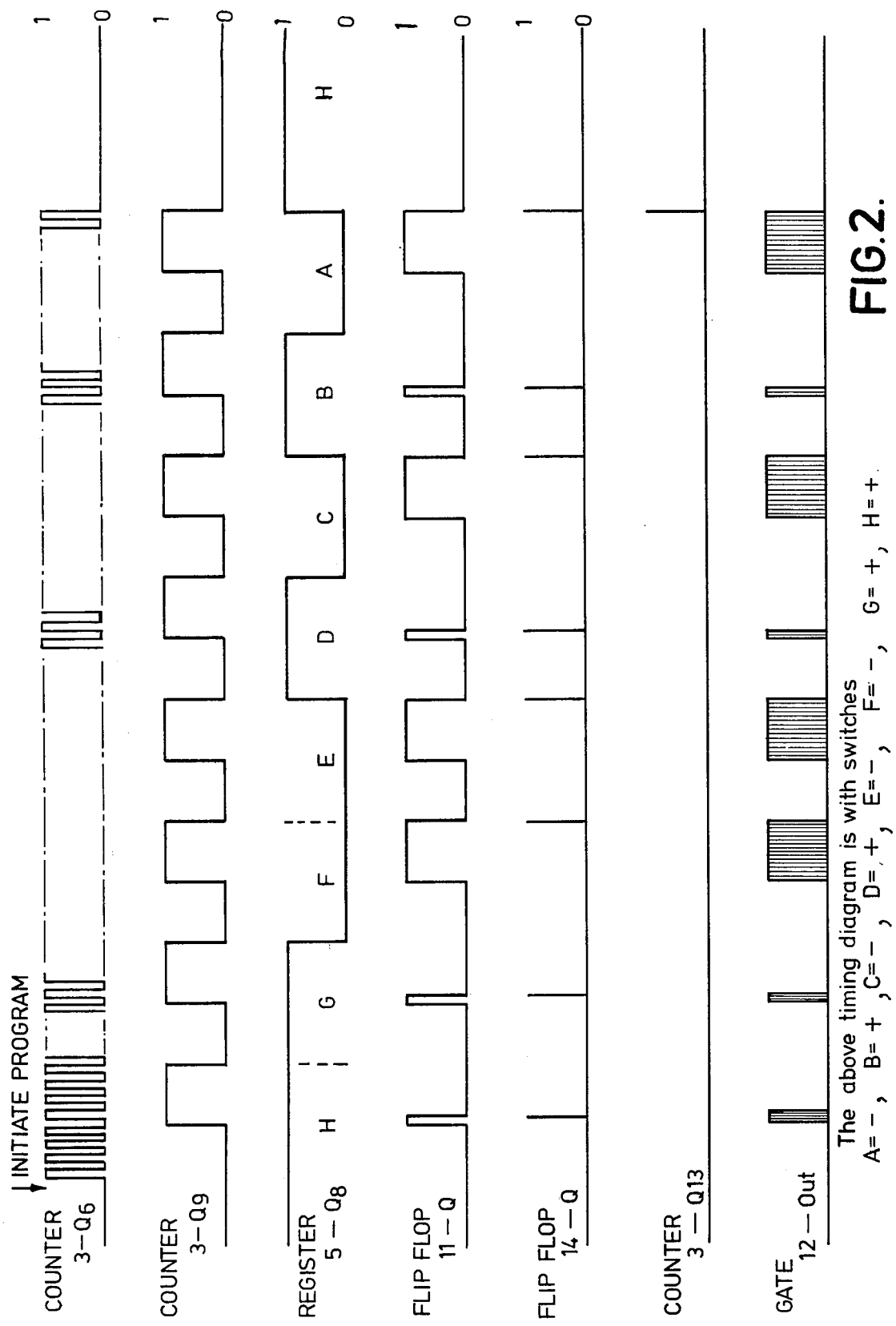
FIG. 2 is a timing diagram for use with FIG. 1.

The operation of the programmer will now be described generally and then in detail with reference also to the timing diagram of FIG. 2, which illustrates the pulses at the positions indicated on FIG. 1.

The pacemaker program transmitted by amplifier/transmitter 13 consists of an eight bit pulse-width modulated signal wherein each pulse is itself several cycles of a sine wave carrier frequency. The pulses of short bit length (which might represent "0" in the pacemaker program) and long bit length ("1") are determined by the signal supplied to NAND gate 12 from flip-flop 11 and are initially generated by the values selected by the settings of the eight switches on the inputs A to H of shift register 5. The carrier frequency present in each pulse is derived from the rapid transitions made by the Q1 stage of counter 3, as supplied to the second input of NAND gate 12. The output of NAND gate 12 is thus the square wave carrier frequency from Q1 modulated by the long or short bit lengths determined by the switching times of flip-flop 11. After passage through amplifier/transmitter 13, this output becomes the tone burst modulated signal described above.

Referring to the operation in more detail, with the press-to-program switch normally open, the monostable 2 output remains high maintaining a reset on counter 3 and disabling oscillator 4.

When it is desired to change the 8-bit program stored in the implanted pacemaker, the values of the 8-bits are selected by providing an appropriate combination of values through opening or closing each of the eight switches on the inputs to shift register 5. In the example given, referring to FIG. 2, the inputs H, G, D, and B are tied to the positive supply bus whereas inputs F, E, C, and A are grounded. This will provide, as to be described, for transmission by amplifier/transmitter 13, the program 00110101 where "0" represents a pulse of short length (and "1" of long length), it being appreciated that the values are transmitted in the sequence HGFEDCBA. This arises since the first value appearing at the Q8 output of shift register 5 is the value of the PI 8 input (H).

To transmit the selected program, the press-to-program switch 1 is depressed. This causes monostable 2 to fire (i.e. causing its output to go low), thus removing the reset from counter 3 and allowing oscillator 4 to commence running at a period $T_O$ determined by its timing components. Counter 3 will increment by 1 count on every negative clock edge provided by oscillator 4.

At a count of Q9, flip-flop 11 clocks the level of its D-input to its Q output, putting Q "high" and $\overline{Q}$ "low". This removes the reset on flip-flop 14 and places its D-input "high". The "high" output of Q is also applied to NAND gate 12 to commence transmission of the first bit in the 8-bit sequence of data. The next positive edge on the clock input of flip-flop 14 will clock its Q output to "high," thus resetting flip-flop 11. The reset of the latter will, in turn, reset flip-flop 14, causing its Q output to go "low" and terminate transmission of the first bit in the 8-bit sequence.

The time at which flip-flop 14 clocks a "high" to its Q output determines the width of the flip-flop 11 Q output and hence the pulse width of the modulation at point C in FIG. 1. It is dependent upon the state of the steering network comprising components 7, 8, 9, and 10. The level on the Q8 output of shift register 5 determines whether the clock pulse for flip-flop 14 arises via NOR gate 7 or 9 and is derived from either the Q6 or Q9 stage of counter 3. With gate 7 enabled, the first positive edge on the flip-flop 14 clock input occurs at $32T_O$ from the time the flip-flop 11 Q output went "high." With gate 9 enabled, this first positive edge occurs at $256T_O$ from the time the flip-flop 11 Q output went "high."

Initially, the Q8 output of shift register 5 represents the value at its H input ("high") and this causes the pulse supplied by flip-flop 11 to NAND gate 12 to be cut off after $32T_O$ (i.e. causing a short pulse representing "0" to be transmitted).

Subsequent bits are then transmitted as the values of the seven remaining shift register stages are sequentially clocked to the Q8 output of shift register 5. The bits are transmitted at each positive transition of the Q9 stage of counter 3 until Q13 is reached. Shift register 5 is clocked on each negative edge of the Q9 stage of counter 3. When the Q13 stage of counter 3 goes high this resets monostable 2 to its initial condition, resets counter 3 and disables the oscillator 4. By this time the values of all eight stages of shift register 5 will have appeared at the Q8 output and the corresponding 8-bits will have been transmitted by amplifier/transmitter 13.

In a typical programmer constructed as described, $T_O$ was set to 0.05 ms: this provided short pulses of 1.6 ms in width and long pulses of 12.8 ms in width. These pulses were each modulated via the Q1 stage of counter 3 at 10 KHz.

The alternative embodiment shown in FIG. 3 will now be described.

Referring to FIG. 3, the programmer again comprises a "press-to-program" switch 1 tied between the electrical supply buses. The switch output drives a monostable 2. The monostable 2 is employed to reset a 13 stage counter 3, to control an oscillator 4, and to reset a decade counter 15. The oscillator 4 includes an "oscillator disable" NOR gate 16 which, when supplied with a high input from monostable 2, provides a low output which disables the oscillator output to a clock input of counter 3.

The Q7, 8 and 9 output stages of counter 3 are combined through a NAND gate 17 and a NOR gate 18 to provide a "short" output pulse to a transmission gate 19. The Q9 output stage of counter 3 provides a "long" output pulse to a transmission gate 20 and, through inverter 21, to the clock input of the decade counter 15.

A NAND gate 22 receives the Q1 output of counter 3 and also the outputs of transmission gates 19 and 20. The output of NAND gate 22 drives an amplifier/transmitter 23, output pulses from which are transmitted into the body for receipt by an implanted programmable cardiac pacemaker where the received pulses are decoded and employed for changing the program stored in the pacemaker.

The Q13 output of counter 3 is supplied to a disable input of monostable 2.

The decade counter 15 has eight output stages (0 to 7) which are successively employed to control (turn on and off) eight transmission gates which, in this embodiment, take the form of two quad/bilateral switches 24. The eight gates formed by the switches 24 each receive an input from a selector switch 25. The switches 25 ("A" to "H") can be individually connected to the positive supply bus or to ground. The eight outputs of the switches 24 are coupled together to provide a common bus 26 which is employed to control transmission gate 20 and (via inverter 27) transmission gate 19.

The operation of the programmer will now be described first generally and then in more detail.

The counts which are supplied by counter 3 to transmission gates 19 and 20 supply pulses representative of short bit lengths (e.g. "0") and long bit lengths (e.g. "1"). The eight bit program desired is selected by setting the switches 25 appropriately and these values are sequentially clocked onto the common bus 26 to open either transmission gate 19 or 20 depending upon the logic value supplied on bus 26. The short or long pulse supplied to the amplifier/transmitter 23 from the opened transmission gate 19 or 20 is employed to modulate the higher frequency count supplied to NAND gate 22 from the Q1 stage of counter 3 so that the output of the amplifier/transmitter is an eight-bit tone burst signal.

Referring to the operation in more detail, with the press to program switch 1 normally open, the monostable 2 output remains high, maintaining a reset on counters 3 and 15 and disabling oscillator 4. No output is provided to amplifier/transmitter 23. When it is desired to change the 8-bit program stored in the implanted pacemaker, the values of the 8-bits are selected by providing an appropriate combination of values through opening or closing each of the switches 25. The press to program switch 1 is then pressed. Pressing, i.e. closing, switch 1 causes monostable 2 to fire (i.e. causing its output to go low), thus removing the reset from the counters 3 and 15 and allowing oscillator 4 to commence running. The removal of the reset to decade counter 15 leaves a count at its "zero" stage, which opens the transmission gate in switches 24 corresponding to switch 25 "A." The output of switch 25 "A" is supplied on common bus 26 and depending on its logic value, opens either transmission gate 19 or 20 thus to supply either a short pulse or a long pulse to NAND gate 22. This short or long pulse modulates the high frequency output of the Q1 stage of counter 3, and is amplified and transmitted by amplifier/transmitter 23.

As soon as the Q9 stage of counter 3 falls, decade counter 15 is incremented by one so that the count, now at its "one" stage, causes the output value supplied by switch 25 "B" rather than 25 "A" to control which of the transmission gates 19 and 20 is opened. The short or long pulse (modulating the Q1 high frequency output as before) is again transmitted by amplifier/transmitter 23.

This cycle repeats for each of the eight switches 25 so that a total of eight tone burst modulated pulses, of either short or long width, is transmitted. Once the eighth pulse has been transmitted, the Q13 stage of counter 3 is then reached to disable monostable 2. This causes the latter to revert to its stable state, which reintroduces a reset to counters 3 and 15 and disables oscillator 4. No further information is hence transmitted until the press to program switch 1 is once again depressed, when the whole cycle would then repeat.

Typically, the oscillator has a 20 KHz frequency. This provides a 10 KHz output at the Q1 stage of counter 3, a pulse length of 3.2 ms to transmission gate 19 (a "short" pulse), a pulse length of 12.8 ms to transmission gate 20 (a "long" pulse), and a data rate for clocking decade counter 15 of 25.6 ms. The NAND gate 22 thus transmits to amplifier/transmitter 23 eight bits, either of 3.2 ms or 12.8 ms in width and each including a 10 KHz square wave carrier.

What is claimed is:

1. An external programmer for generating an output signal comprising a fixed number of pulses each having a preselected duration, said output signal being supplied to an implanted, programmable body function apparatus for varying given operational functions thereof, comprising:
   register means for receiving and storing a fixed number of logic bits, each of said logic bits determining the duration of one of the fixed number of pulses in said output signal;
   pulse generation means for generating a pulse signal at a predetermined frequency;
   counter means coupled to said pulse generation means having a plurality of pulse outputs of different fixed durations, the duration of one of said pulse outputs being less than that of the remaining pulse outputs, the durations of the remaining pulse outputs corresponding to preselected durations of the pulses comprising said output signal as determined by said logic bits;
   output means for transmitting said output signal to said implanted apparatus;
   control means coupling said counter means to said output means for periodically enabling said output means to transmit the fixed number of pulses in said output signal at a rate corresponding to the duration of said one pulse output of said counter means; and
   logic means coupled to said counter means and said register means for disabling said output means after each periodic enabling thereof, the duration of each pulse in said output signal being determined by said remaining pulse outputs from said counter means.

2. A programmer according to claim 1 wherein the duration of each of the pulses in said output signal has either a first or second value corresponding to a first or second logic bit received by said register means; and said counter means has first, second and third pulse outputs wherein said first output periodically enables said output means to transmit the fixed number of pulses in said output signal at a rate corresponding to the duration of said first pulse output, and said logic means couples either said second or third pulse output from said counter means to said output means, after each periodic enabling thereof, to disable said output means, the duration of the pulses in said output signal having said first value when said output means is disabled by the second pulse output from said counter means and having said second value when said output means is disabled by the third pulse output of said counter means.

3. A programmer according to claim 2 wherein said logic means comprises at least two transmission gates, said counter means suplying inputs to said gates and the outputs supplied to said output means by said gates being controlled by said fixed number of logic bits.

4. A programmer according to claim 3 wherein said control means for enabling said output means comprises a first flip-flop, and said logic means further comprises a second flip-flop for disabling said output means thereby controlling the duration of the pulses in said output signal.

5. A programmer according to claim 1 wherein said pulse generating means comprises:
   programmer activating switch means;
   monostable means, energized by said switch means, for resetting said counter after the fixed number of pulses in said output signal has been generated; and
   oscillator means, enabled by said monostable means, for providing a clock signal to said counter.

* * * * *